United States Patent [19]

Futter

[11] Patent Number: 4,472,623
[45] Date of Patent: Sep. 18, 1984

[54] CONTACT LENS HEATING DEVICE

[75] Inventor: Menachem Futter, Staten Island, N.Y.

[73] Assignee: Barnes-Hind/Hydrocurve, Inc., Sunnyvale, Calif.

[21] Appl. No.: 568,002

[22] Filed: Jan. 4, 1984

[51] Int. Cl.³ ............................ H05B 3/06; A61L 2/04
[52] U.S. Cl. ..................................... 219/521; 219/328;
219/386; 219/430; 219/439; 219/441; 219/505;
219/530; 338/22 R; 422/307
[58] Field of Search .............. 219/214, 328, 385, 386,
219/419, 430, 433, 437, 438, 439, 441, 451, 521,
505, 530, 540; 422/38, 199, 292, 300, 301, 302,
307; 70/DIG. 10; 292/DIG. 66; 338/22 R, 22 SD

[56] References Cited

U.S. PATENT DOCUMENTS

| | | |
|---|---|---|
| 3,983,362 | 9/1976 | Hoogesteger et al. ............. 219/521 |
| 3,996,447 | 12/1976 | Bouffard et al. ................... 219/505 |
| 4,044,226 | 8/1977 | Kadlecik et al. ................... 219/521 |
| 4,158,126 | 6/1979 | Seitz .................................... 219/439 |
| 4,165,359 | 8/1979 | Thomas et al. .................... 422/105 |
| 4,242,572 | 12/1980 | Thomas et al. .................... 219/521 |
| 4,256,952 | 3/1981 | Thomas et al. .................... 219/521 |
| 4,307,289 | 12/1981 | Thomas et al. .................... 219/521 |
| 4,331,859 | 5/1982 | Thomas et al. .................... 219/521 |
| 4,369,355 | 1/1983 | Helixon .............................. 219/521 |
| 4,379,965 | 4/1983 | Dounce et al. .................... 219/521 |

Primary Examiner—Volodymyr Y. Mayewsky

[57] ABSTRACT

Heat to disinfect contact lens is supplied uniformly to a well in which the lenses are placed, from a single small heat source by providing an area of high resistance to heat flow directly above the heat source.

9 Claims, 3 Drawing Figures

CONTACT LENS HEATING DEVICE

BACKGROUND OF THE INVENTION

This invention relates to the heat disinfection of contact lenses.

Contact lenses collect microorganisms which, if permitted to grow, can infect the eye of the wearer. Consequently, it is necessary to clean and disinfect the lens, preferably daily, to kill microorganisms on the lens. This necessity is especially pronounced with soft contact lenses, which are made of material that is permeable to water and into which microorganisms can penetrate.

One known method of disinfecting a contact lens comprises immersing the lens in an aqueous medium, typically a buffered saline solution, and heating the immersed lens at a moderately elevated temperature (e.g. 80° C.–95° C.) for enough time, typically at least 10 minutes, to kill any microorganisms that may be present in or on the lens. The heating is carried out in a small device whose basic elements include a chamber for holding the case that contains the immersed lens, and a heating element that heats the chamber.

It is highly desirable to maintain a relatively uniform temperature throughout the chamber, so that even if the location of the lens-carrying case shifts within the chamber the lenses will be heated sufficiently and will not be heated to too high a temperature. This objective becomes more pronounced as the shapes and sizes of lens-carrying cases proliferate; since the chamber should be designed to be able to accommodate as many such shapes and sizes as possible, any lens case smaller than the largest case that can fit into the chamber will be capable of moving about within the chamber if the unit is bumped. It becomes necessary to heat the chamber sufficiently hot that the lenses are disinfected regardless of where they are located in the chamber. If the actual heating element is smaller than the chamber, this can lead to the area of the chamber closest to the element being so hot that the lens can be damaged.

Prior art units have dealt with this problem by heating the chamber through a heating block which absorbs a significant quantity of heat from an electrical-resistance heating element and releases the absorbed heat gradually to the chamber. The operation is controlled by a thermostat which shuts off the heating element when the block reaches a predetermined temperature, i.e. has absorbed a predetermined quantity of heat, substantially before the end of the disinfecting cycle. This type of system has several drawbacks. The heating element must be large enough as to heating capacity and as to physical size to heat the block sufficiently in an acceptable short length of time while maintaining a relatively uniform temperature across the top of the block. In addition, the block must be relatively large and dense, which fact adds to the weight of the unit and increases the expense of making and shipping the unit. Discontinuing the application of heat before the disinfection cycle ends requires that the lenses be heated to a temperature at least as high as the preferred disinfection temperature range, at which point the element is shut off; this exposes the lenses to temperatures that could be unacceptably close to temperatures at which the lenses would be damaged. Since most of the disinfection is performed while heat is dissipated from the block without additional heat input from the element, operation is vulnerable to loss of heat from the block to unexpectedly cool ambient atmosphere, to premature opening of the unit by the operator, and the like. The chamber is actually in the optimum temperature range for only a brief period; otherwise the chamber is cooler.

Illustrative of such units are those described in U.S. Pat. No. 4,044,226 and U.S. Pat. No. 4,307,289. Both patents disclose heat disinfection units that include a heating block having relatively high heat absorptive ability, and a thermostatic switch that shuts off the application of heat from the heating element to the block a substantial length of time before the disinfection cycle is complete. U.S. Pat. No. 4,044,226 actually discourages the use of a timing circuit. In addition, U.S. Pat. No. 3,983,362 describes a similar principle of operation, and even discourages using a "heat member" which gives up absorbed heat rapidly, on the ground that the interior of the carrying case cannot be maintained at an acceptable temperature.

The present invention avoids these and other drawbacks and presents the advantages discussed below, by employing components (e.g. a timing circuit, and a thin plate rather than a heating block) which the prior art teaches away from.

SUMMARY OF THE INVENTION

The present invention comprises a unit for the heat disinfection of contact lenses, comprising
 (a) means defining a housing that contains a well having a heat-conductive, substantially flat bottom and having a shape adapted for receiving a case for holding in side-by-side relationship a pair of contact lenses;
 (b) means located below the well for heating the well to a disinfection temperature, said means including heating element means,
  plate means in heat-conducting contact with said heating element means and said well bottom for conveying heat from said element means to said well bottom, wherein said element means is disposed below said plate means and has a horizontal cross-sectional area less than half that of said plate means, and
  means located between said plate means and said well for dispersing heat in said plate means, comprising a region of lower specific heat conductivity than said plate means, at least part of which region is directly above said element means, which is effective on generation of heat by said element means to form on said well bottom a temperature profile in which the region of highest temperature does not cover the center of said element and in which the difference in the temperatures of any two points on the surface of the well bottom is no more than 15° C.;
 (c) circuit means for heating said element means by passing current therethrough upon activation of the circuit means, and for discontinuing the passage of said current a predetermined length of time after said activation, wherein said length of time is sufficient to disinfect said lenses; and
 (d) switch means for activating said circuit means.

DETAILED DESCRIPTION OF THE INVENTION

The present invention is intended to provide improved uniformity of temperature within the lens heating unit, while employing a heating element much smaller than the unit.

Figure 1:
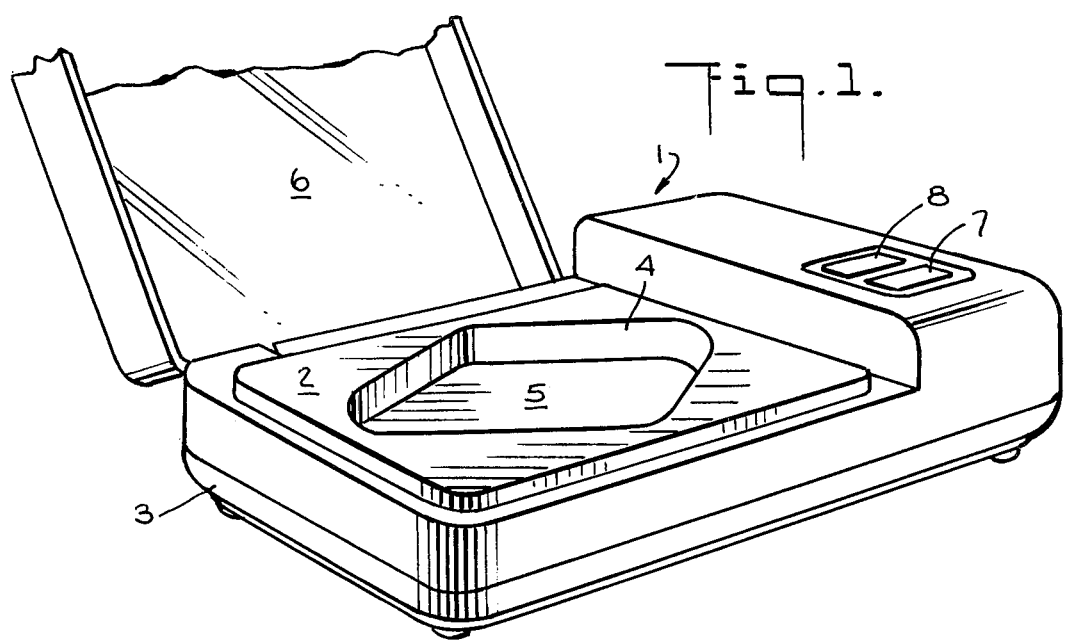
FIG. 1 is a perspective view of the exterior of a heating unit embodying the present invention.

Referring to the drawings, FIG. 1 shows the exterior of a typical heat disinfecting unit in which the present invention can be embodied. Housing 1 is formed by assembling top 2 to base 3 by screws (not shown) passing through holes in base 3 which are screwed into sockets formed in the interior of the top 2. Well 4 is formed in top 2 and can have the shape depicted or any other shape capable of accommodating a conventional lens case of the type that holds a pair of contact lenses in side-by-side relationship immersed in a storage solution. Such cases are frequently oblong in shape, as a result of which well 4 has a generally oblong shape. The case can also be circular; to accommodate such a case well 4 is wider (as measured from the front to the back of housing 1) than it would have to be to hold only an oblong case. The bottom 5 of well 4 is flat. Bottom 5 can be made of plastic material, as can the rest of housing 1, provided that well bottom 5 conducts heat.

Housing 1 also includes lid 6, hinged to the back of top 2 and adapted to cover well 4 when a lens case is placed into well 4 to be heated. Switch 7 protrudes through top 2 to be accessible to the user. As will be discussed below, pressing switch 7 activates the heating and timing mechanism for disinfection of lenses. If desired, a light bulb can be provided to indicate that the unit is heating; the bulb is visible through optional lens 8. Top 2, base 3, lid 6, switch 7 and lens 8 can all be made of plastic.

Figure 2:
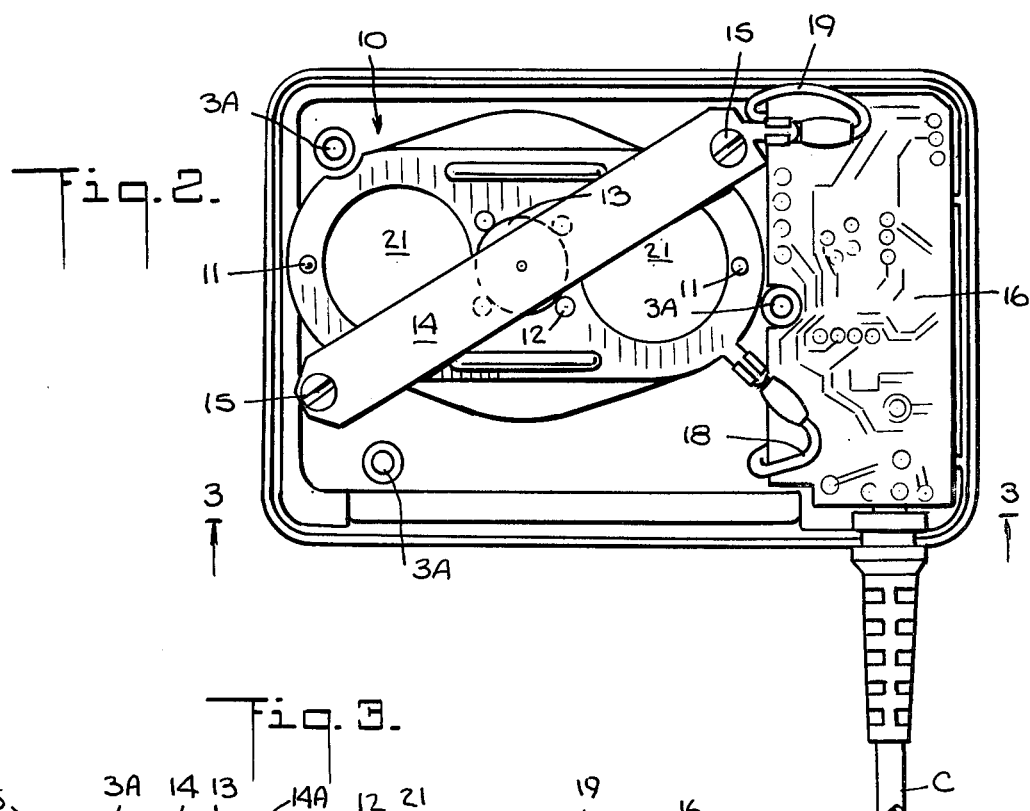
FIG. 2 is a view from beneath the interior of the unit shown in FIG. 1.

The details of the heating means of the present invention can be seen in FIG. 2, which is the view one sees upon inverting the unit of FIG. 1 and removing bottom 3. The bottom surface 9 of well 4 can be seen but is partially obscured by heating plate means 10 which extends across much of the underside of well 4. Plate 10 is held against horizontal sliding by pegs 11 protruding from surface 9 through holes formed in plate 10. Plate 10 is generally flat, and is thin relative to its width and length as will be seen better in FIG. 3. Plate 10 also includes lugs 12; four such lugs are satisfactory for the purpose discussed below, although three to eight such lugs will work as well. Plate 10 should be made of material which conducts electricity and which has relatively high heat conductivity, but need not have a high specific heat capacity. A preferred material of construction for plate 10 is cold-rolled steel.

Heating element 13 is in heat-conductive and electricity-conductive contact with plate 10. Element 13 is held against horizontal sliding by the lugs 12 which are formed in plate 10. The element fits snugly between the lugs. Element 13 can be optionally attached by a medium such as a cement or grease which will not melt at the temperatures that element 13 reaches during a heat disinfection cycle. Element 13 is any of several conventional models, generally known as positive temperature coefficient (PTC) heat elements, which increase rapidly in temperature when an electric current is passed through them, and which attain a uniformly high temperature across the surface of the element that is in contact with plate 10. One material known to exhibit this property is lanthanum-doped barium titanate. Further description appears in U.S. Pat. No. 3,996,447 to Bouffard et al. The element depicted in FIG. 2 is one such model, about the size of a dime, sold by Murata Manufacturing Co., Shiga 527 Japan.

Element 13 can be larger than the one shown, so long as it is smaller in cross-sectional area than the bottom 5 of well 4; but the advantages of the present invention are realized if element 13 is less than half, less than one-fourth, or even less than one-tenth the cross-sectional area of bottom 5. Element 13 is preferably centered on bottom 5, to make a uniform temperature easier to maintain, although it can be located elsewhere on the bottom of plate 10. This element should be capable of attaining a temperature of about 130° C. to about 150° C., preferably about 140° C., so that lenses held inside the well 4 can be heated to at least 80° C. It should be noted that the invention works quite satisfactorily with even a single element 13.

Figure 3:
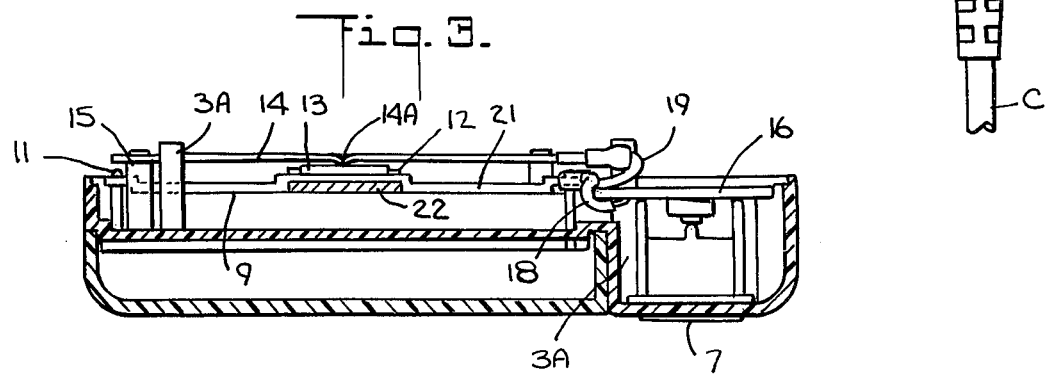
FIG. 3 is a cross-sectional view of the same unit, taken along the line 3—3 of FIG. 2.

Strip 14 extends across element 13, between the two posts 15 whose tops are preferably level with the top surface of element 13. Strip 14 is held in place by screws screwed into the posts 15. Strip 14 must be electrically conductive and can be a flat strip of metal, such as cold-rolled steel, but need not be spring steel. Good electrical contact between strip 14 and element 13 is necessary, and can be ensured by forming a small bead 14A as shown in FIG. 3. Bead 14A is of the size that could be formed by holding a nail point to the other side of strip 14 and tapping the nail head once with a hammer hard enough to form the bead but not hard enough to make a hole in strip 14.

Circuit means 16 is located adjacent to well 4 in top 2, and includes cord C leading to a household power source. Switch 7, which activates circuit 16, is not seen in this view. Leads 18 and 19 conduct electricity from circuit 16 to, respectively, plate 10 and strip 14 to which they are connected by soldering or by mechanical crimping about lugs formed in plate 10 and strip 14.

Circuit means 16 must be capable of supplying current to element 13 (through leads 16 and 18, strip 14, and plate 10) when switch 7 is activated, and of discontinuing the current flow automatically after the passage of a preset period of time from the activation of the switch. It is well within the ability of the ordinary skilled electrical engineer to assemble such a circuit. One such circuit is a conventional type known as an "R-C" circuit which contains resistor(s) and capacitor(s) arranged so that closing the circuit (as by pressing on switch 7) causes current to flow through the circuit for a period of time that is a function of the size of the resistor(s) and the capacitor(s). At the end of that period of time, current stops flowing through the circuit until the circuit is again closed. In the unit depicted in FIG. 2, after cord C is plugged into a normal wall outlet, closing circuit means 16 causes current to flow through the electrical circuit formed by lead 18, plate 10, element 13, strip 14, and lead 19. Element 13 becomes hot and the heat it produces is conducted to plate 10 and thence to well 4. Current should be supplied to element 13 for a predetermined time of 10–20 minutes, preferably 10–15 minutes, and should be on long enough to heat contact lenses, which are immersed in storage solution in a lens case in well 4, to at least 80° C. and should remain on for over half the total disinfection period during which the lenses are at or above 80° C.

After the various elements depicted in FIG. 2 are assembled as indicated, base 3 is attached, such as by screws driven into holes 3A formed in the underside of top 2.

FIG. 3 is a cross-sectional view of the unit as assembled in FIG. 2, and shows better the novel arrangement of the present invention. Lid 6, well 4, plate 10, heating element 13, strip 14, posts 15, and leads 18 and 19 are as described for FIG. 2. It can be clearly seen that plate 10 includes areas 21, which directly contact the bottom of well 4. An air space 22 above element 13 is thus formed between areas 21. Space 22 comprises a means for dispersing heat around the region of plate 10 that is directly over element 13. Preferably, a temperature profile is formed on well surface 9 in which the area of highest temperature is not over the center of element 13, and more preferably not over element 13 at all. Thus, only a part of what is in the normal position of use the top surface of plate 10 directly contacts the surface 9 of well 4. Heat flows more readily through the material of which plate 10 is made, but must flow farther to reach areas 21; on the other hand, heat has a shorter distance to flow to reach the region of well 4 that is exposed to air space 22, but the air in that space poses a significant resistance to heat flow. The result is that the flow of heat from element 13 to well 4, and therefore the temperature at any point of the bottom 5 of well 4, is more uniform; that is, there is less variation between the temperature of any two points on the bottom of well 4.

For a given maximum temperature of element 13, the dimensions of air space 22 and any additional holes, if any, in plate 10 should be arranged so that the temperature maintained across the bottom surface 5 of well 4 is as uniform as possible. Preferably, the maximum temperature difference between any two points of surface 5 while the heating element is generating heat is 15° C., and more preferably is 10° C. Maximum differences of 8° or 9° C. have been observed. Thus, the current can be left on for at least half of the disinfection cycle, ensuring that a consistent flow of heat, and a consistent temperature that is safe for the lenses, are maintained to well 4.

By way of further exemplification, plate 10 and well 4 can be about 3¼ inches long and 1½ inches wide, and plate 10 is about four-hundredths of an inch thick. Areas 21 are spaced one on each side element 13, are about one inch in diameter, and protrude about two-hundredths of an inch above the rest of the surface of plate 10. As indicated, the plate 10 should not retain significant amount of heat. Preferably, the unit should maintain the temperature within well 4 at at least 80° C. (for proper disinfection of the lens) but no higher than about 95° C. (to avoid harming the lens or evaporating the solution in which it is immersed). The temperature of the lenses in well 4 should be maintained above 80° C. for at least 10 minutes, preferably up to 15-20 minutes. More preferably, the well bottom temperature is about 85°-90° C., and the difference between the highest and lowest temperatures on the well bottom is no more than 10° C. It is also preferred that the plate 10 underlie at least two-thirds of the well bottom, and that the plate is centered with respect to the well, and the element is centered with respect to the well and the plate.

It will be recognized that the embodiment described above is exemplary, and that there are other equivalent alternatives for various aspects of the unit. For instance, the unit need not be a top-loading model like the one shown in FIG. 1, but can be loaded from the side by means of a drawer or platform that slides or swings out from the housing. In addition, plate 10 can be circular, with the raised area 21 comprising a circular band which contacts the well 4; in this case, the cross-sectional view of plate 10 taken along any radius would appear as shown in FIG. 3.

In a preferred alternative, one to twenty small holes are drilled into a plate 10 to assist the dispersion of heat flowing away from element 13. Moreover, the areas 21 need not be circular, and there can be up to 10 or 20 small areas 21 rather than the two depicted in the Figures.

What is claimed is:

1. A unit for the heat disinfection of contact lenses, comprising
    (a) means defining a housing that contains a well having a heat-conductive, substantially flat bottom and having a shape adapted for receiving a case for holding in side-by-side relationship a pair of contact lenses;
    (b) means located below the well for heating the well to a disinfection temperature, said means including a single heating element means,
        plate means in heat-conducting contact with said heating element means and said well bottom for conveying heat from said element means to said well bottom, wherein said element means is disposed below said plate means and has a horizontal cross-sectional area less than half that of said plate means, and
        means located between said plate means and said well for dispersing heat in said plate means, comprising a region of lower specific heat conductivity than said plate means, at least part of which region is directly above said element means, which is effective on generation of heat by said element means to form on said well bottom a temperature profile in which the region of highest temperature does not cover the center of said element and in which the difference in the temperatures of any two points on the surface of the well bottom is no more than 15° C.;
    (c) circuit means for heating said element means by passing current therethrough upon activation of the circuit means, and for discontinuing the passage of said current a predetermined length of time after said activation, wherein said length of time is sufficient to disinfect said lenses; and
    (d) switch means for activating said circuit means.

2. The unit of claim 1 wherein said plate means underlies at least two-thirds of said well bottom and is centered with respect thereto, and said element means is centered with respect to said plate means and said well.

3. The unit of claim 1 wherein said means for dispersing heat comprises an air gap over said element means and regions of said plate means symmetrically located on each side of said air gap which directly contact said well bottom.

4. The unit of claim 1 wherein said well and said plate means are elongated in shape.

5. The unit of claim 1 wherein said predetermined length of time is 10 minutes to 20 minutes.

6. The unit of claim 1 wherein following activation of said switching means the temperature in said well is at 80° to 95° C. for at least 10 minutes.

7. The unit of claim 1 wherein the cross-sectional area of said element means is no more than one-tenth that of said well bottom.

8. The unit of claim 1 wherein said means for dispersing heat comprises one to twenty holes through said plate means.

9. The unit of claim 1 wherein following activation of said circuit means the temperature of said well bottom is 85°-90° C. and the difference in the temperature of any two points on the surface of the well bottom is no more than 10° C.

* * * * *